United States Patent [19]
Dueholm et al.

[11] Patent Number: 5,970,116
[45] Date of Patent: Oct. 19, 1999

[54] METHOD OF DETERMINING THE DENSITY PROFILE OF A PLATE-SHAPED MATERIAL

[75] Inventors: Sten Dueholm, Copenhagen; Steen Teller, Birkerød, both of Denmark

[73] Assignee: Wesser & Dueholm, Copenhagen K, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,835
[22] PCT Filed: Jun. 15, 1995
[86] PCT No.: PCT/DK95/00242
§ 371 Date: Dec. 19, 1996
§ 102(e) Date: Dec. 19, 1996
[87] PCT Pub. No.: WO95/35491
PCT Pub. Date: Dec. 28, 1995

[30] Foreign Application Priority Data

Jun. 20, 1994 [DK] Denmark .................... 0723/94

[51] Int. Cl.⁶ .................................................. G01N 9/24
[52] U.S. Cl. .................................. 378/90; 378/54
[58] Field of Search .................... 378/86, 89, 88, 378/90, 51, 53, 54

[56] References Cited

U.S. PATENT DOCUMENTS

| | | | |
|---|---|---|---|
| 4,047,029 | 9/1977 | Allport | 250/273 |
| 4,123,654 | 10/1978 | Reiss et al. | 378/90 X |
| 4,228,351 | 10/1980 | Snow et al. | 250/273 |
| 4,918,712 | 4/1990 | Le Floc'h et al. | 378/89 |
| 4,956,856 | 9/1990 | Harding | 378/89 X |
| 5,195,116 | 3/1993 | Le Floc'h et al. | 378/89 |
| 5,195,117 | 3/1993 | Ong | 378/89 |
| 5,247,561 | 9/1993 | Kotowski | 378/89 X |

FOREIGN PATENT DOCUMENTS

| | | |
|---|---|---|
| 1202431 | 3/1986 | Canada . |
| 4243454 | 3/1994 | Germany . |

*Primary Examiner*—David P. Porta
*Attorney, Agent, or Firm*—Jacobson, Price, Holman & Stern, PLLC

[57] ABSTRACT

A method of non-destructively, on-line determining the density profile in a plate-shaped material with a density which varies discretely or continuously over the plate thickness, while the density at a specific depth of the plate is assumed to be constant, such as for instance plates based on wood, by means of X-rays or gamma rays from a source placed on one side of the plate. Two detectors are placed on the other side of the plate, one detector measuring in the emitting direction of the source and the other detector measuring in the other direction and being movable relative to the plate. The counting number of the second detector is adjusted by means of the counting number of the first detector. By a suitable choice of emitting direction and detecting direction it is possible to provide a measurement of the density in a specific measuring volume merely by dividing the counting number of the second detector by the counting number of the first detector. As a result, the attenuation in the material is left out. The angle of incidence must be substantially identical with the angle of reflection.

18 Claims, 3 Drawing Sheets

METHOD OF DETERMINING THE DENSITY PROFILE OF A PLATE-SHAPED MATERIAL

FIELD OF THE INVENTION

The invention relates to a method of determing the density profile of a plate-shaped material of a density varying discretely or continuously over the plate thickness, while the density at a specific depth of the plate is assumed to be preferably constant, such as for instance plates based on wood, by means of X-rays or gamma rays from a source placed on one side of the plate.

BACKGROUND ART

Such a detection may for instance, but not exclusively be used by the production of plates based on wood and manufactured by a gluing together of wood particles of a varying size, i.e. plywood made of individual layers, OSB (Oriented Strand Boards) made of large strips of wood, chipboards (made of a mat of layers of large and small chips usually separated in layers), and fibreboards made of wood fibres.

By the manufacture of these plates, a thermosetting glue is applied onto the particles, said glue being laid out or scattered on plates or tapes in the form of a laminated or homogenous mat and subsequently subjected to a continuous or non-continuous process in a hot press so as to be pressed or cured.

The parameters of the process and especially the characteristics of the press have an effect on the typical properties of the completed plate. The latter is particularly obvious in connection with the density profile of the plate, i.e. the variation of the density over the thickness which accordingly is an indicator of both the operating conditions of the production plant and of the use properties of the plate.

According to the prior art it is possible to destructively determine the density profile on laboratory tests, either gravimetrically by way of a milling off and weighing in layers or by way of an isotope-transmission scanning on a test sample in the plane of the plate. Based on these results, the process can be adjusted, but not without involving a time-delay of at least 1 to 2 hours.

A demand exists for a possibility of performing a non-destructive, on-line-determination of the density profile in the plate in such a manner that it is possible to adjust the process very quickly, typically in a few minutes without interrupting said process and without involving a sampling and laboratory tests.

German Patent specification No. 4,243,454 discloses a way of measuring the density profile along the edge of a plate by means of a pencil of rays and a plurality of detectors arranged below the plate. The pencil of rays is obliquely emitted inwards from the side along the edge of the plate. A resulting advantage is that nothing but the attenuation in the lowermost layer is measured by means of a first portion of said pencil of rays, whereafter the attenuation in the lowermost and the lowermost but one layer is measured by means of another part of said pencil of rays, etc. Subsequently, it is possible to calculate the attenuation in each layer. This method is, however, encumbered with the draw-back that it is too unreliable. In addition, it only involves a measuring along the edge, which is not always sufficiently representative.

U.S. Pat. No. 5,195,116 discloses an apparatus for detecting the layers of separation in a laminated plate by means of X-rays. A narrow pencil of X-rays is scattered as the consequence of the compton-effect. A detector directed towards a measuring volume detects the radiation scattered therefrom, said radiation representing the electron density and consequently the density in the measuring volume. A displacement of the source and the detector, respectively, in an up and downward direction relative to the plate renders it possible to obtain information on the structure of the layers and on possible errors in the material. This measuring system is, however, encumbered with the draw-back that the signal and the scattered radiation intensity from a specific measuring volume beyond the density also depend on the thickness and density of all the superposed layers. These values can be determined in principle. The latter would, however, require extensive Calibration measurings on known articles. In addition, possible measuring errors are accumulated from all individual layers to the instant measuring volume.

BRIEF DESCRIPTION OF THE INVENTION

The object of the present invention is to provide a method of determining the density profile of a plate-shaped material, which is independent of the instant distribution of the density and which accordingly only involves a minimum of calibration.

A method of the above type is according to the invention characterised in that at least two detectors arranged on the other side of the preferably endless plate advanced below the measuring device in the longitudinal direction, whereby a first detector is placed in the emitting direction of the source and measures the radiation transmitted through the plate, and that at least one detector is placed outside the emitting direction of the source and measures the scattered radiation from partial volumes along the emitting direction of the source, the second detector being displaced relative to the plate at the same time as the detecting direction of the second detector is maintained.

In this manner a suitable choice of emitting direction and detecting direction renders it possible to provide a measurement of the density in a specific measuring volume merely by dividing the counting number of the second detector by the the counting number of the first detector. As a result, the attenuation in the material is left out.

The second and movable detector may according to the invention optionally be replaced by a mechanically idle array of detectors, where the individual detectors in the array detect measuring values simultaneously or succeedingly during the movement of the plate.

BRIEF DESCRIPTION OF THE DRAWINGS

The invention is explained in greater detail below with reference to the accompanying drawings, in which.

BEST MODE FOR CARRYING OUT THE INVENTION

Figure 1:
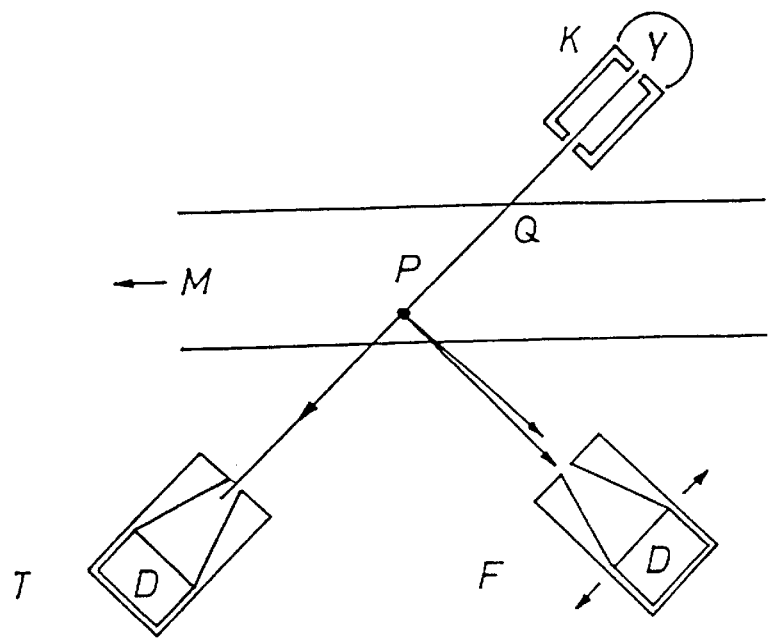
FIG. 1 illustrates how the source and the detectors are arranged relative to the plate by the method according to the invention.

FIG. 1 illustrates how the method according to the invention renders it possible both to measure transmitted and to measure forwardly scattered (Compton-scattered) radiation. X-ray and gamma radiation is preferably scattered as a consequence of the Compton-effect from the electrons of the atoms in all directions apart from isotropically. In response to the scattering angle θ the following terms are often used, viz. "Back-Scatter" for (θ≧90°) and "Forward-Scatter" for (θ≧90°). The measuring technique uses the term "Back-Scatter" or backscattered radiation for measuring situations in which the source and the detector are placed on the same side of the measuring target irrespective of the scattering angle which can be less than 90°. Correspondingly, the term "Forward-Scatter" or forward radiation is used for measuring situations in which the source and the detector are placed on their respective side of the measuring target. The present invention can only be carried out provided the source and the detectors are placed on their respective side of a typical, plate-shaped measuring target. As far as the field of application is concerned, the invention is therefore limited compared to the well-known "Back-Scatter" techniques, but within the limited field of application, viz. the plate-shaped materials, the method according to the invention renders it possible to obtain a measuring signal which is proportional to the density in a partial volume irrespective of the densities and thicknesses of the surrounding layers.

In FIG. 1 K is a radioactive source or an X-ray tube emitting radiation towards a detector T which measures the radiation transmission through a plate M. A detector F is collimated such that it only receives scattered radiation from a small partial volume about a scattering location P. The detector F can be displaced such that the observed scattering location P is displaced along the line P-Q.

As far as plate-shaped materials are concerned, the density of which only varies substantially perpendicular to the plane of the plate M, the needle-shaped pencil of rays can in principle be replaced by a fan-shaped pencil of rays. Consequently, the locations P and Q can be considered elongated measuring volumes perpendicular to the plane of the drawing. In this manner a very strong measuring signal is obtained for a specific source intensity. Then the collimator in front of the detector F need only be structured such that it comprises a visual field exceeding the maximum width of the fan-shaped pencil of rays in the plate M.

The detector F can comprise several movable detectors in order to obtain a more intense measuring sensitivity, or more movable detectors can scan partial areas in such a manner that a complete density profile is obtained very quickly or in such a manner that only the areas being most interesting from a productional point of view are examined. The examination of interesting partial areas is an exact property which is only obtained by the method according to the invention. The known "Back-Scatter"-principles necessitate a measuring of all partial areas between the surface and the desired measuring area in order to allow a calculation of the distribution of the density at a specific depth of the plate.

Figure 2:
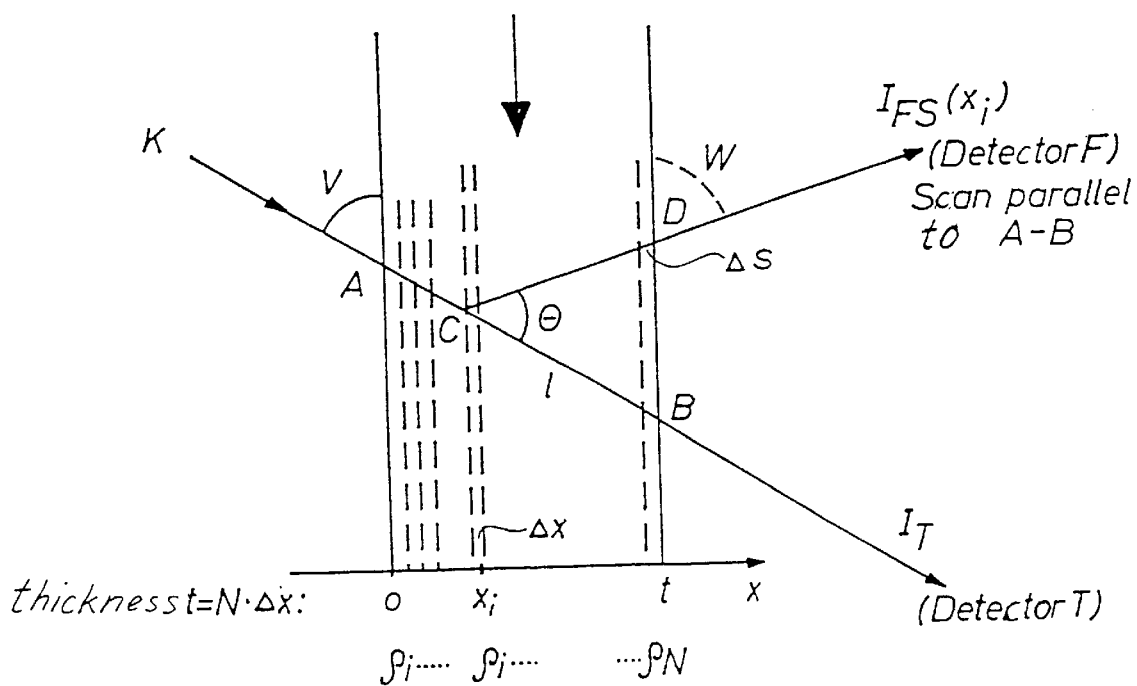
FIG. 2 illustrates how the measuring of the density profile is optimized by a suitable choice of emitting direction and detecting directions relative to the plate.

FIG. 2 illustrates how the density profile is mathematically derived from the measured sizes. K, T and F have the same meaning as in FIG. 1, and here they are only illustrated in form of emitting directions. M is the plate typically moving below the contact-free measuring. The density varies continuously or discretely perpendicular to the plane of the plate M, here indicated as an X-axis. The radiation from the source K meets the plate M at the location A below an angle of incidence on V. In the observing location C the radiation is scattered, and the detector F detects only the portion of the scattered radiation which is scattered at an angle θ. The angle of reflection is designated W. The emitted beam exits the plate M at B, and the observed scattered beam exits the plate M at D.

When it is assumed, that it is a discrete density distribution, the intensity of the radiation beam $I_{FS}$ from a volume element $V_i$ at $X_i$ can be expressed as $I_{FS}(X_i)=$ $$I_{FS}(X_i) = I_o \cdot e^{-\mu \Delta X \cdot \alpha_1 \cdot \sum_{p=1}^{i} \rho_p} \cdot S_i \cdot e^{-\mu' \Delta X \cdot \alpha_2 \cdot \sum_{p=i+1}^{N} \rho_p} \quad (1)$$

where $$S_i = \sigma(\theta, E) \cdot \rho_i \cdot V_i \cdot \epsilon_D$$

$$\alpha_1 = \frac{1}{\sin V}; \quad \alpha_2 = \frac{1}{\sin(180 - \theta - V)} = \frac{1}{\sin(\theta + V)}$$

The equation includes the intensity of the radiation $I_O$ of the source K, the attenuation along A-C, the attenuation along C-D, where the coefficient of absorption $\mu' > \mu$, as the energy E' of the Compton-scattered radiation is lower than the energy E of the primary radiation from the source K. $S_i$ includes the scattering probability σ depending on the energy E and the scattering angle θ as well as on the density $\rho_i$ in the volume element $V_i$, the size thereof as well as a combined solid angle and efficiency factor $\epsilon_D$ for the detector F.

An insertion of the identity $\mu'\alpha_2 = \mu'\alpha_2 + \mu\alpha_1 - \mu\alpha_1$ implies that $$I_{FS}(X_i) = I_o \cdot e^{-\mu \Delta X \cdot \alpha_1 \cdot \sum_{1}^{N} \rho_p} \cdot S_i \cdot e^{(\mu \alpha_1 - \mu' \cdot \alpha_2) \Delta X \sum_{i+1}^{N} \rho_p} \quad (2)$$

$$\text{or} \quad I_{FS}(x_i) = T \cdot S_i \cdot K.$$

The factor T is indeed recognized to be the intensity of the emitted radiation found at $I_T = I_O \cdot E^{-\mu <\rho> \cdot L}$, where $$\langle \rho \rangle = \frac{1}{N} \sum \rho_i$$

is the average density of the plate, and $L = t/\sin V = t \cdot \alpha_1 = N \cdot \Delta x \cdot \alpha_1$ is the travelling length of the beam in the plate M.

The expression K is 1 for $\mu \alpha_1 = \mu' \alpha_2$, which is obtained for $$\frac{\sin(V + \theta)}{\sin V} = \frac{\mu'}{\mu} > 1$$

The equation is as mentioned due to the Compton-relation E'=

$$\frac{E}{1 + \frac{E}{M_0 C^2}(1 - \cos\theta)}$$

In other words, E'<E and consequently $\mu' > \mu$ for a very large area of radiating energies and materials.

The density in volume elements $V_i$ for K=1 is in other words determined by the proportion $I_{FS}(x_i)/I_T$ independent of the density profile. The parameters forming part of $S_i$, are apparatus constants, σ(θ, E) being found at the radiation energy E and the scattering angle θ is determined by the cross-section of the beam, and the collimator and $\epsilon_D$ are found at the collimator opening, the efficiency of the detector, and the distance between the detector and the scattering location.

The angular relation can alternatively be expressed by the fact that the distance CD must be shorter than the distance CB (which must be the same attenuation of the radiation along these paths. The coefficient of absorption is, however, higher along CD).

The angle of incidence V must therefore always be less than 90°.

E'<E implies that $\mu'>\mu$. As $\mu<1$, it is in many cases possible to choose $\mu'\cdot\alpha=\mu$, whereby the density in the observed volume $V_i$ can be expressed by the measured radiation intensities $I_T$ and $I_{FS}$. Two solutions apply as $\mu=\Delta S/\Delta X$ is symmetrical about V=45°. In practice, $\theta=90°$ is chosen to be the angle providing the best solution. The energy of the primary beam must, however, always be chosen such relative to the thickness, the average density, and the composition of the measuring target that the attenuation is approximately 10 to 70% which corresponds to $0.1<\mu\rho_M t<1$. One has for instance for a material with $\rho_M$ almost equal to 1 g/cm$^3$ and t=2 cm, the equation 0.05 cm$^2$/g<$\mu$<0.5 cm$^2$/g. A gamma source K with an energy of 60 keV or an X-ray source with an anode applied a voltage of 100 keV corresponding to a photon energy of approximately 70 keV turned out to be suitable for materials-based on wood or plastics ($\mu$=0.165 cm$^2$/g for carbon at 70 keV). In connection with a suited scattering angle $\theta$=90°, the following equation is found for E=70 keV $$E' = \frac{70}{1+\frac{70}{511}\cdot 1} = 62 \text{ keV}$$

The change in $\mu$ can be found by consulting tables to be approximately 0.01 cm$^2$/g, of which $$\frac{\mu'}{\mu} = \frac{0,174}{0,165} = 1,05$$

The above is met by the angular relation provided the angle of incidence V=43.5°. When the angle of incidence V is chosen to be 45°, the corresponding scattering angle is $\theta$=87°.

A complete angular relation means in other words $I_{FS}$ ($X_i$)=$I_T\cdot S_i\cdot 1$ with $S_i=\sigma\cdot\rho_i\cdot V_i\cdot\epsilon_D$ or $\rho_i$=constant·

$$\rho_i = \text{constant} \cdot \frac{I_{FS}(X_i)}{I_T}$$

When tests are performed with V=45°, the used scattering angle $\theta$ should be 87°, as mentioned above, instead of 90°. The difference is, however, almost irrelevant, and moreover, an effect justifies a scattering angle of 90°.

When an X-ray tube is used instead of a gamma source, a beam-hardening takes place forwards through the material which corresponds to the average energy in the location B, cf. FIG. 2, being slightly higher than the average energy of the radiation in the location A. The scattering probability $\sigma$ in the location B is therefore slightly less likely in the location A. Conversely, the correcting factor $$K = \exp[(\mu\alpha_1 - \mu'\alpha_2)\cdot\Delta X \cdot \sum_{L+1}^{N}\rho_p = 1$$

in the location B ($\Sigma$=remaining plate weight for scattered radiation=0) and a few percentages lower in the location A. In practice, these effects neutralize one another more or less, and usually $\theta$=90° is chosen instead of $\theta$=87°. Under all circumstances, the effects are insignificant, and the image is not changed although several slot collimators are used which means that a larger angular interval is covered.

Figure 3:
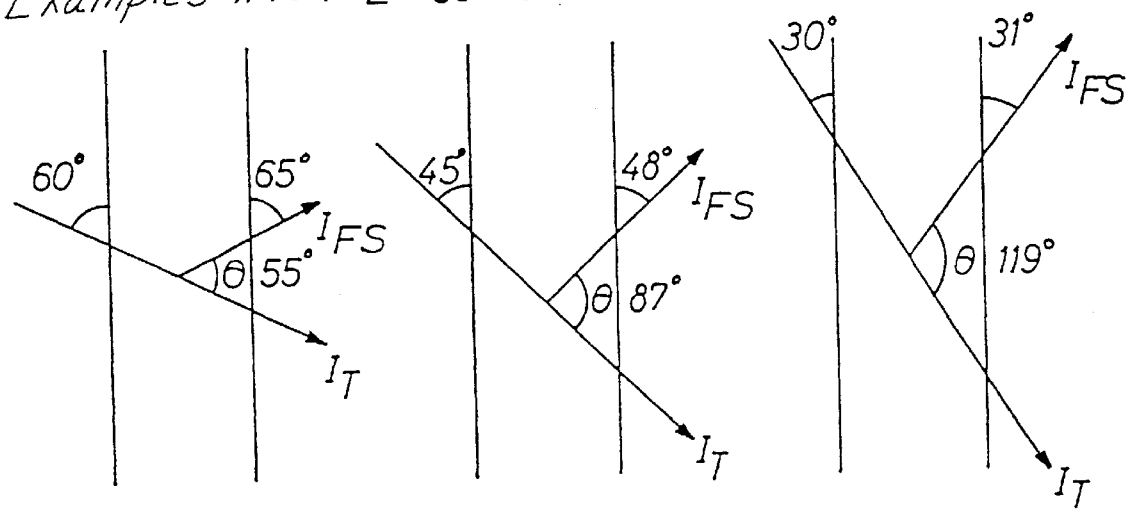
FIG. 3 illustrates various optimum choices of the emitting direction and the detecting directions of some plate materials.
Figure 4:
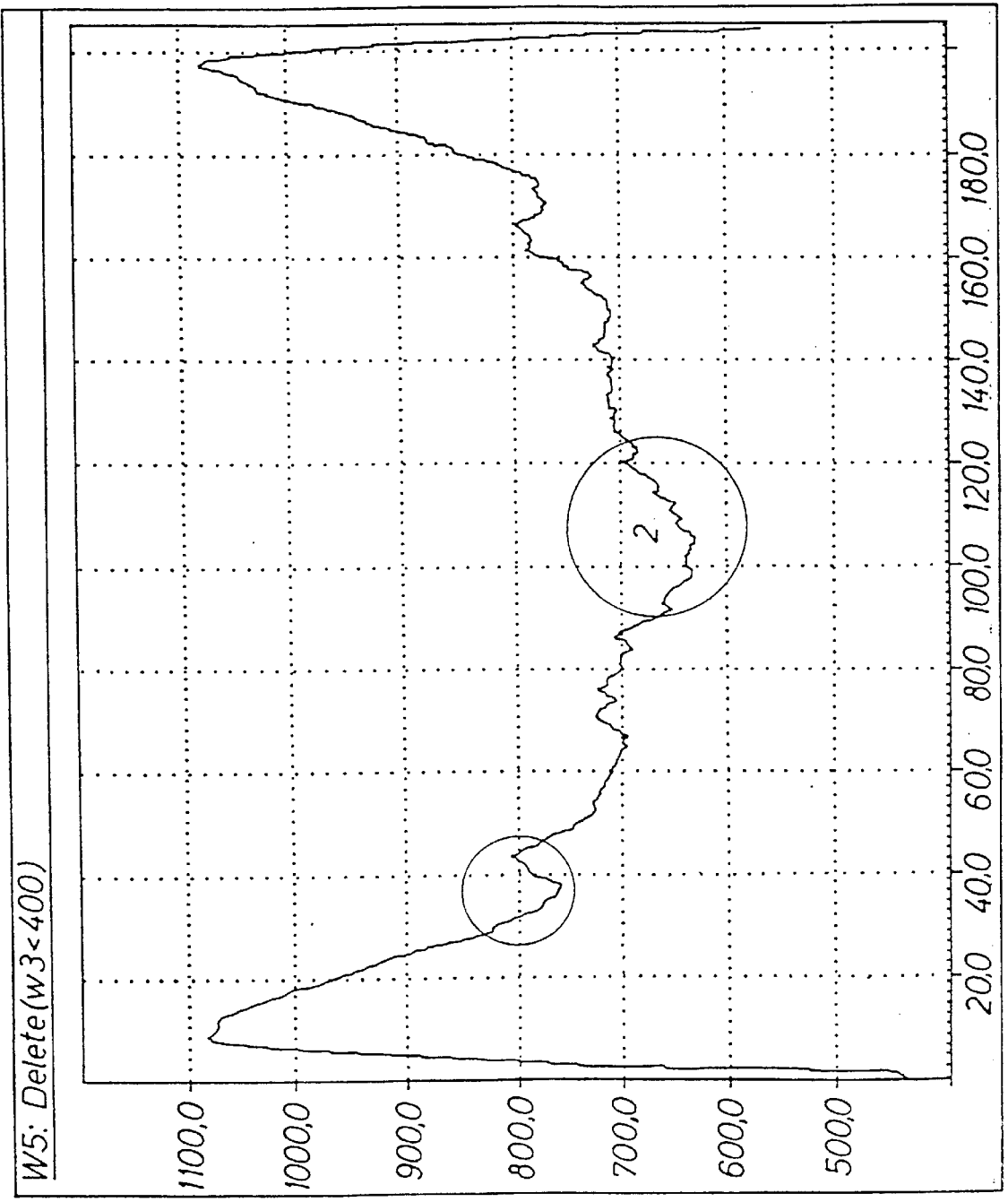
FIG. 4 illustrates an example of a density profile provided by means of the method according to the invention.

As far as light materials are concerned, energies of 50 to 100 keV are, as mentioned, advantageously used, where the Compton-change is low and the coefficient of absorption for $I_{FS}$ is therefore only a few percentages higher than for $I_T$. Therefore the angular relation stipulates that the angle of reflection W must almost be equal to the angle of incidence V. Examples of the latter appear from FIG. 3.

The invention is based on a combination of scattered and transmitted radiation through a plate-shaped material with a varying density over the thickness, whereby it is possible by a suitable choice of angles and radiation energy to obtain a calibration-free measuring of the density profile.

The target in question is not necessarily plate-shaped. It can also be of other shapes, such as wedge-shaped or shaped with a curved surface.

We claim:

1. A method of determining the density profile of a plate-shaped material M of a density varying discretely or continuously across the plate thickness, while the density at a specific depth of the plate is substantially constant, by means of X-rays or gamma rays from a source K placed on one side of the plate M, comprising at least a first detector T and a second detector F arranged on the other side of the plate M advanced through the measuring device in the longitudinal direction, whereby the first detector T is placed in the emitting direction of the source K and measures the radiation transmitted through the plate M, and the at least one second detector F is placed outside the emitting direction of the source K and measures the scattered radiation from partial volumes along the emitting direction of the source K, the second detector F being displaced relative to the first detector T while the detecting direction is maintained, wherein the detecting direction of the second detector F is chosen relative to the emitting direction of the source K in such a manner that the density is expressed directly as a proportion between the radiation measured by each of the first and second detectors, and an angle of incidence V between the emitting direction and the plate M is almost identical with an angle of reflection W between the plate and the second detector.

2. The method according to claim 1, wherein the angle of incidence between the emitting direction and the plate is substantially identical with but smaller than the angle of reflection between said plate and the second detector so as to obtain the same attenuation between the scattered and the non-scattered radiation, even if the scattered radiation has a smaller energy.

3. The method according to claim 1, wherein the angle of incidence between the emitting direction and the plate is different from the angle of reflection between said plate and the second detector so as to obtain the same attenuation between the scattered and the non-scattered radiation.

4. The method according to claim 1, wherein the angle of incidence between the emitting direction and the plate is smaller than the angle of reflection between said plate and the second detector so as to obtain the same attenuation between the scattered and the non-scattered radiation, even if the scattered radiation has a smaller energy.

5. The method according to claim 1, wherein the angle of incidence between the emitting direction and the plate is approximately equal to the angle of reflection between said plate and the second detector so as to obtain the same attenuation between the scattered and the non-scattered radiation.

6. The method as claimed in claim 1, wherein the angle of incidence V is at least approximately 60°, whereas the angle of reflection W is at least approximately 65°.

7. A method as claimed in claim 1, characterized in that the angle of incidence V, between the emitting direction and the plate is approximately 45°, whereas the angle of reflection W, between the plate and the second detector, is approximately 48°.

8. The method as claimed in claim 1, characterised in that the angle of incidence V is approximately 30°, whereas the angle of reflection W is approximately 31°.

9. The method as claimed in claim 1, characterised in that the detecting direction of the second detector F is approximately 87° relative to the emitting direction of the source K when said emitting direction forms an angle of approximately 45° with the surface of the plate.

10. The method as claimed in claim 9 where the radiation source K used is an X-ray tube, characterised in that a compensation for beam-hardening is carried out.

11. The method according to claim 1, wherein the angle of incidence between the emitting direction and the plate is substantially identical with but different from the angle of reflection between said plate and the second detector so as to obtain the same attenuation between the scattered and the non-scattered radiation.

12. A method of determining the density profile of a plate-shaped material of a density varying discretely or continuously across the plate thickness, while the density at a specific depth of the plate is substantially constant, by means of X-rays or gamma rays from a source placed on one side of the plate, comprising at least a first detector and a second detector arranged on the other side of the plate advanced through the measuring device in the longitudinal direction, whereby the first detector is placed in the emitting direction of the source and measures the radiation transmitted through the plate, and the second detector is placed outside the emitting direction of the source and measures the scattered radiation from partial volumes along the emitting direction of the source, the second detector being displaced relative to the first detector and parallel to the emitting direction of the source, while the detecting direction is maintained, wherein the detecting direction of the second detector is chosen relative to the emitting direction of the source in such a manner that the density is expressed directly as a proportion between the radiation measured by the first and second detectors, and an angle of incidence between the emitting direction and the plate is almost identical with an angle of reflection between the plate and the second detector.

13. The method as claimed in claim 12, wherein the angle of incidence is at least approximately 60° whereas the angle of reflection is at least approximately 65°.

14. A method as claimed in claim 12, wherein the angle of incidence, between the emitting direction and the plate is approximately 45°, whereas the angle of reflection, between the plate and the second detector, is approximately 48°.

15. A method as claimed in claim 12, wherein the angle of incidence is approximately 30°, whereas the angle of reflection is approximately 31°.

16. The method according to claim 12, wherein the angle of incidence between the emitting direction and the plate is different from the angle of reflection between said plate and the second detector so as to obtain the same attenuation between the scattered and the non-scattered radiation.

17. The method according to claim 12, wherein the angle of incidence between the emitting direction and the plate is smaller than the angle of reflection between said plate and the second detector so as to obtain the same attenuation between the scattered and the non-scattered radiation, even if the scattered radiation has a smaller energy.

18. The method according to claim 12, wherein the angle of incidence between the emitting direction and the plate is approximately equal to the angle of reflection between said plate and the second detector so as to obtain the same attenuation between the scattered and the non-scattered radiation.

* * * * *